United States Patent
Johnson et al.

(10) Patent No.: US 8,735,644 B2
(45) Date of Patent: *May 27, 2014

(54) BIOCOMPATIBLE WOUND DRESSING

(75) Inventors: Royce Johnson, San Antonio, TX (US); David Tumey, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/332,246

(22) Filed: Dec. 20, 2011

(65) Prior Publication Data

US 2012/0095421 A1  Apr. 19, 2012

Related U.S. Application Data (63) Continuation of application No. 12/828,117, filed on Jun. 30, 2010, now Pat. No. 8,084,664, which is a continuation of application No. 11/409,116, filed on Apr. 21, 2006, now Pat. No. 7,763,769, which is a continuation of application No. 10/075,743, filed on Feb. 14, 2002, now Pat. No. 7,070,584.

(60) Provisional application No. 60/269,657, filed on Feb. 16, 2001.

(51) Int. Cl.
*A61F 13/00* (2006.01)
*A61M 35/00* (2006.01)

(52) U.S. Cl.
USPC .......... 602/48; 602/41; 602/42; 602/46; 604/289; 604/290; 604/304

(58) Field of Classification Search
USPC ............ 602/41–43, 46, 48, 2; 604/289, 290, 604/313, 304–308
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986); pp. 94-96 (certified translation).

(Continued)

*Primary Examiner* — Kim M Lewis (57) ABSTRACT

A biocompatible wound dressing comprised of a pad for insertion substantially into a wound site and wound drape for sealing enclosure of the foam pad at the wound site. The pad, comprised of a foam or other like material having relatively few open cells in contact with the areas upon which cell growth is to be encouraged so as to avoid unwanted adhesions, but having sufficiently numerous open cells so that drainage and negative pressure therapy may continue unimpaired, is placed in fluid communication with a vacuum source for promotion of fluid drainage, as known in the art. The pad is further comprised of an ultra-low density fused-fibrous ceramic, or a bioabsorbable branched polymer, or cell growth enhancing matrix or scaffolding.

20 Claims, 1 Drawing Sheet

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,118,470 A | 10/1978 | Casey et al. |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,595,713 A | 6/1986 | St. John |
| 4,605,399 A | 8/1986 | Weston et al. |
| 4,608,041 A | 8/1986 | Nielson |
| 4,614,794 A | 9/1986 | Easton et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,837,015 A | 6/1989 | Olsen |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,904,260 A | 2/1990 | Ray et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,077,049 A | 12/1991 | Dunn et al. |
| 5,085,861 A | 2/1992 | Gerhart et al. |
| 5,086,170 A | 2/1992 | Luheshi et al. |
| 5,092,858 A | 3/1992 | Benson et al. |
| 5,100,396 A | 3/1992 | Zamierowski |
| 5,102,983 A | 4/1992 | Kennedy |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,256,418 A | 10/1993 | Kemp et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,303,719 A | 4/1994 | Wilk et al. |
| 5,324,519 A | 6/1994 | Dunn et al. |
| 5,342,376 A | 8/1994 | Ruff |
| 5,344,415 A | 9/1994 | DeBusk et al. |
| 5,358,494 A | 10/1994 | Svedman |
| 5,368,859 A | 11/1994 | Dunn et al. |
| 5,437,622 A | 8/1995 | Carion |
| 5,437,651 A | 8/1995 | Todd et al. |
| 5,447,725 A | 9/1995 | Damani et al. |
| 5,449,383 A | 9/1995 | Chatelier et al. |
| 5,487,897 A | 1/1996 | Polson et al. |
| 5,527,293 A | 6/1996 | Zamierowski |
| 5,549,584 A | 8/1996 | Gross |
| 5,556,375 A | 9/1996 | Ewall |
| 5,578,662 A | 11/1996 | Bennett et al. |
| 5,599,552 A | 2/1997 | Dunn et al. |
| 5,607,388 A | 3/1997 | Ewall |
| 5,621,035 A | 4/1997 | Lyles et al. |
| 5,622,707 A | 4/1997 | Dorigatti et al. |
| 5,629,186 A | 5/1997 | Yasukawa et al. |
| 5,636,643 A | 6/1997 | Argenta et al. |
| 5,645,081 A | 7/1997 | Argenta et al. |
| 5,674,192 A | 10/1997 | Sahatijan et al. |
| 5,711,957 A | 1/1998 | Patat et al. |
| 5,711,958 A | 1/1998 | Cohn et al. |
| 5,717,030 A | 2/1998 | Dunn et al. |
| 5,759,570 A | 6/1998 | Arnold |
| 5,780,281 A | 7/1998 | Yasukawa et al. |
| 5,795,584 A | 8/1998 | Totakura et al. |
| 5,824,335 A | 10/1998 | Dorigatti et al. |
| 5,834,188 A | 11/1998 | Harada et al. |
| 5,902,874 A | 5/1999 | Roby et al. |
| 5,902,875 A | 5/1999 | Roby et al. |
| 5,914,387 A | 6/1999 | Roby et al. |
| 5,932,716 A | 8/1999 | Sampath |
| 5,951,295 A | 9/1999 | Lyles et al. |
| 5,997,568 A | 12/1999 | Liu |
| 6,001,117 A | 12/1999 | Huxel et al. |
| 6,040,431 A | 3/2000 | Keck et al. |
| 6,071,267 A | 6/2000 | Zamierowski |
| 6,083,524 A | 7/2000 | Sawhney et al. |
| 6,087,479 A | 7/2000 | Stamler et al. |
| 6,090,544 A | 7/2000 | Harada et al. |
| 6,093,388 A | 7/2000 | Ferguson |
| 6,103,491 A | 8/2000 | Sampath |
| 6,110,460 A | 8/2000 | Sampath |
| 6,135,116 A | 10/2000 | Vogel et al. |
| 6,136,333 A | 10/2000 | Cohn et al. |
| 6,187,047 B1 | 2/2001 | Kwan et al. |
| 6,200,606 B1 | 3/2001 | Peterson et al. |
| 6,241,747 B1 | 6/2001 | Ruff |
| 6,255,277 B1 | 7/2001 | Stamler et al. |
| 6,287,316 B1 | 9/2001 | Agarwal et al. |
| 6,316,523 B1 | 11/2001 | Hyon et al. |
| 6,345,623 B1 | 2/2002 | Heaton et al. |
| 6,352,709 B1 | 3/2002 | Stamler et al. |
| 6,383,478 B1 | 5/2002 | Prokop et al. |
| 6,387,391 B1 | 5/2002 | Shikinami et al. |
| 6,395,293 B2 | 5/2002 | Polson et al. |
| 6,407,060 B1 | 6/2002 | Charette et al. |
| 6,471,978 B1 | 10/2002 | Stamler et al. |
| 6,479,643 B1 | 11/2002 | Keck et al. |
| 6,488,643 B1 | 12/2002 | Tumey et al. |
| 6,491,693 B1 | 12/2002 | Lytinas |
| 6,493,568 B1 | 12/2002 | Bell et al. |
| 6,498,142 B1 | 12/2002 | Sampath et al. |
| 6,514,534 B1 | 2/2003 | Sawhney |
| 6,521,223 B1 | 2/2003 | Calias et al. |

(56) References Cited

U.S. PATENT DOCUMENTS

| | | |
|---|---|---|
| 6,553,998 B2 | 4/2003 | Heaton et al. |
| 6,565,871 B2 | 5/2003 | Roser et al. |
| 6,566,345 B2 | 5/2003 | Miller et al. |
| 6,579,533 B1 | 6/2003 | Törmälä et al. |
| 6,599,518 B2 | 7/2003 | Oster et al. |
| 6,692,773 B2 | 2/2004 | Burrell et al. |
| 6,696,499 B1 | 2/2004 | Cohn et al. |
| 6,713,083 B1 | 3/2004 | McGregor et al. |
| 6,726,923 B2 | 4/2004 | Iyer et al. |
| 6,780,890 B2 | 8/2004 | Bassler et al. |
| 6,814,079 B2 | 11/2004 | Heaton et al. |
| 6,893,424 B2 | 5/2005 | Shchervinsky |
| 6,913,589 B2 | 7/2005 | Dextradeur et al. |
| 6,932,974 B2 | 8/2005 | Bezwada et al. |
| 6,939,568 B2 | 9/2005 | Burrell et al. |
| 6,989,156 B2 | 1/2006 | Gillis |
| 7,008,647 B2 | 3/2006 | Burrell et al. |
| 7,025,990 B2 | 4/2006 | Sawhney |
| 7,041,868 B2 * | 5/2006 | Greene et al. .................. 602/48 |
| 7,052,708 B2 | 5/2006 | O'Leary |
| 7,070,584 B2 | 7/2006 | Johnson |
| 7,074,412 B2 | 7/2006 | Weber |
| 7,166,570 B2 | 1/2007 | Hunter et al. |
| 7,182,758 B2 | 2/2007 | McCraw |
| 7,201,925 B2 | 4/2007 | Gillis |
| 7,202,281 B2 | 4/2007 | Cohn et al. |
| 7,216,651 B2 | 5/2007 | Argenta et al. |
| 7,241,736 B2 | 7/2007 | Hunter et al. |
| 7,244,444 B2 | 7/2007 | Bates |
| 7,255,881 B2 | 8/2007 | Gillis et al. |
| 7,265,098 B2 | 9/2007 | Miller et al. |
| 7,294,334 B1 | 11/2007 | Michal et al. |
| 7,294,350 B2 | 11/2007 | Marraccini |
| 7,306,903 B1 | 12/2007 | Sampath et al. |
| 7,326,426 B2 | 2/2008 | Nathan et al. |
| 7,342,048 B2 | 3/2008 | Miyaji et al. |
| 7,351,250 B2 | 4/2008 | Zamierowski |
| 7,361,168 B2 | 4/2008 | Makower et al. |
| 7,390,497 B2 | 6/2008 | DesNoyer et al. |
| 7,700,819 B2 | 4/2010 | Ambrosio et al. |
| 7,763,769 B2 | 7/2010 | Johnson et al. |
| 8,084,664 B2 | 12/2011 | Johnson et al. |
| 2001/0000728 A1 | 5/2001 | Sawhney et al. |
| 2001/0009662 A1 | 7/2001 | Cohn et al. |
| 2001/0012511 A1 | 8/2001 | Bezwada et al. |
| 2001/0029956 A1 | 10/2001 | Argenta et al. |
| 2001/0041743 A1 | 11/2001 | Offenbacher et al. |
| 2001/0043943 A1 | 11/2001 | Coffey |
| 2001/0055622 A1 | 12/2001 | Burrell et al. |
| 2002/0001608 A1 | 1/2002 | Polson et al. |
| 2002/0010150 A1 | 1/2002 | Cortese et al. |
| 2002/0028181 A1 | 3/2002 | Miller et al. |
| 2002/0055721 A1 | 5/2002 | Palasis et al. |
| 2002/0072798 A1 | 6/2002 | Riesle et al. |
| 2002/0077661 A1 | 6/2002 | Saadat |
| 2002/0107223 A1 | 8/2002 | Oster et al. |
| 2002/0115951 A1 | 8/2002 | Norstrem et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0193336 A1 | 12/2002 | Elkins et al. |
| 2003/0003127 A1 | 1/2003 | Brown et al. |
| 2003/0027744 A1 | 2/2003 | Dana et al. |
| 2003/0028140 A1 | 2/2003 | Greff |
| 2003/0039697 A1 | 2/2003 | Zhao et al. |
| 2003/0060752 A1 | 3/2003 | Bergheim et al. |
| 2003/0072783 A1 | 4/2003 | Stamler et al. |
| 2003/0077242 A1 | 4/2003 | Sawhney |
| 2003/0077311 A1 | 4/2003 | Vyakarnam et al. |
| 2003/0096734 A1 | 5/2003 | Dehazya et al. |
| 2003/0108511 A1 | 6/2003 | Sawhney |
| 2003/0113359 A1 | 6/2003 | Iyer et al. |
| 2003/0118651 A1 | 6/2003 | Jampani et al. |
| 2003/0125230 A1 | 7/2003 | Cohen et al. |
| 2003/0135148 A1 | 7/2003 | Dextradeur et al. |
| 2003/0152522 A1 | 8/2003 | Miller et al. |
| 2003/0152546 A1 | 8/2003 | Shalaby |
| 2003/0211793 A1 | 11/2003 | Bell et al. |
| 2003/0232087 A1 | 12/2003 | Lawin et al. |
| 2004/0001872 A1 | 1/2004 | Shih et al. |
| 2004/0006311 A1 | 1/2004 | Shchervinsky |
| 2004/0023842 A1 | 2/2004 | Pathak et al. |
| 2004/0037836 A1 | 2/2004 | Stamler et al. |
| 2004/0039415 A1 | 2/2004 | Zamierowsky |
| 2004/0063606 A1 | 4/2004 | Chu et al. |
| 2004/0063612 A1 | 4/2004 | Yalpani |
| 2004/0093026 A1 | 5/2004 | Weidenhagen et al. |
| 2004/0097402 A1 | 5/2004 | Bassler et al. |
| 2004/0101564 A1 | 5/2004 | Rioux et al. |
| 2004/0127475 A1 | 7/2004 | New et al. |
| 2004/0127843 A1 | 7/2004 | Tu et al. |
| 2004/0142888 A1 | 7/2004 | Manne et al. |
| 2004/0156819 A1 | 8/2004 | Cohn et al. |
| 2004/0180829 A1 | 9/2004 | Bassler et al. |
| 2004/0197409 A1 | 10/2004 | Iyer et al. |
| 2004/0208845 A1 | 10/2004 | Michal et al. |
| 2004/0213756 A1 | 10/2004 | Michal et al. |
| 2004/0217146 A1 | 11/2004 | Beck |
| 2004/0253203 A1 | 12/2004 | Hossainy et al. |
| 2004/0265475 A1 | 12/2004 | Hossainy et al. |
| 2005/0008609 A1 | 1/2005 | Cohn et al. |
| 2005/0019303 A1 | 1/2005 | Tsai et al. |
| 2005/0027265 A1 | 2/2005 | Maki et al. |
| 2005/0042197 A1 | 2/2005 | Shalaby |
| 2005/0048121 A1 | 3/2005 | East et al. |
| 2005/0063937 A1 | 3/2005 | Li et al. |
| 2005/0106119 A1 | 5/2005 | Brandom et al. |
| 2005/0107756 A1 | 5/2005 | McCraw |
| 2005/0112087 A1 | 5/2005 | Musso et al. |
| 2005/0112186 A1 | 5/2005 | Devore et al. |
| 2005/0129624 A1 | 6/2005 | Burrell et al. |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159364 A1 | 7/2005 | Cooper |
| 2005/0159697 A1 | 7/2005 | Dextradeur et al. |
| 2005/0163822 A1 | 7/2005 | Shirahama et al. |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0175667 A1 | 8/2005 | Carlyle |
| 2005/0177190 A1 | 8/2005 | Zamierowski |
| 2005/0182445 A1 | 8/2005 | Zamierowski |
| 2005/0186247 A1 | 8/2005 | Hunter et al. |
| 2005/0187268 A1 | 8/2005 | Von Rechenberg et al. |
| 2005/0191248 A1 | 9/2005 | Hunter et al. |
| 2005/0208094 A1 | 9/2005 | Armitage et al. |
| 2005/0234510 A1 | 10/2005 | Zamierowski |
| 2005/0238683 A1 | 10/2005 | Adhikari et al. |
| 2005/0240147 A1 | 10/2005 | Makower et al. |
| 2005/0240220 A1 | 10/2005 | Zamierowski |
| 2005/0244363 A1 | 11/2005 | Hossainy et al. |
| 2005/0245906 A1 | 11/2005 | Makower et al. |
| 2005/0249697 A1 | 11/2005 | Uhrich et al. |
| 2005/0255079 A1 | 11/2005 | Santerre et al. |
| 2005/0255082 A1 | 11/2005 | Santerre et al. |
| 2005/0266086 A1 | 12/2005 | Sawhney |
| 2005/0271617 A1 | 12/2005 | Shirahama et al. |
| 2005/0277577 A1 | 12/2005 | Hunter et al. |
| 2006/0024266 A1 | 2/2006 | Brandom et al. |
| 2006/0035861 A1 | 2/2006 | Berg et al. |
| 2006/0051394 A1 | 3/2006 | Moore et al. |
| 2006/0052743 A1 | 3/2006 | Reynolds |
| 2006/0057179 A1 | 3/2006 | Giroux |
| 2006/0067908 A1 | 3/2006 | Ding |
| 2006/0115449 A1 | 6/2006 | Pacetti |
| 2006/0120994 A1 | 6/2006 | Cotton et al. |
| 2006/0135912 A1 | 6/2006 | Chernomorsky et al. |
| 2006/0140904 A1 | 6/2006 | Wellisz et al. |
| 2006/0142736 A1 | 6/2006 | Hissink et al. |
| 2006/0147409 A1 | 7/2006 | Pathak et al. |

(56) References Cited

U.S. PATENT DOCUMENTS

| | | |
|---|---|---|
| 2006/0147412 A1 | 7/2006 | Hossainy et al. |
| 2006/0148958 A1 | 7/2006 | Haraguchi et al. |
| 2006/0153796 A1 | 7/2006 | Fitz |
| 2006/0177416 A1 | 8/2006 | Turnell et al. |
| 2006/0177417 A1 | 8/2006 | Musso et al. |
| 2006/0188545 A1 | 8/2006 | Hadba |
| 2006/0198815 A1 | 9/2006 | Barker et al. |
| 2006/0216323 A1 | 9/2006 | Knaack et al. |
| 2006/0240063 A9 | 10/2006 | Hunter et al. |
| 2006/0240064 A9 | 10/2006 | Hunter et al. |
| 2006/0251612 A1 | 11/2006 | Kotzev et al. |
| 2006/0263330 A1 | 11/2006 | Emeta et al. |
| 2006/0280720 A1 | 12/2006 | Fitz et al. |
| 2006/0286063 A1 | 12/2006 | Shebuski et al. |
| 2006/0292077 A1 | 12/2006 | Zhao |
| 2007/0014752 A1 | 1/2007 | Roy et al. |
| 2007/0025955 A1 | 2/2007 | Lowinger et al. |
| 2007/0116666 A1 | 5/2007 | Cohn et al. |
| 2007/0128152 A1 | 6/2007 | Hadba et al. |
| 2007/0128153 A1 | 6/2007 | Hadba et al. |
| 2007/0128154 A1 | 6/2007 | Hadba et al. |
| 2007/0128155 A1 | 6/2007 | Seyedin et al. |
| 2007/0218124 A1 | 9/2007 | Devore et al. |
| 2007/0219497 A1 | 9/2007 | Johnson et al. |
| 2007/0225663 A1 | 9/2007 | Watt et al. |
| 2007/0237750 A1 | 10/2007 | Naughton |
| 2007/0248643 A1 | 10/2007 | Devore et al. |
| 2007/0248676 A1 | 10/2007 | Stamler et al. |
| 2007/0265585 A1 | 11/2007 | Joshi et al. |
| 2007/0265586 A1 | 11/2007 | Joshi et al. |
| 2007/0275033 A9 | 11/2007 | Moore et al. |
| 2007/0280899 A1 | 12/2007 | Williams et al. |
| 2008/0003253 A1 | 1/2008 | Clauser |
| 2008/0003299 A1 | 1/2008 | Trotter et al. |
| 2008/0004368 A1 | 1/2008 | Wang et al. |
| 2008/0004578 A1 | 1/2008 | Hixon et al. |
| 2008/0014170 A1 | 1/2008 | Hnojewyj et al. |
| 2008/0014286 A1 | 1/2008 | Gillis et al. |
| 2008/0019969 A1 | 1/2008 | Gorman |
| 2008/0031918 A1 | 2/2008 | Lawin et al. |
| 2008/0031919 A1 | 2/2008 | Henson et al. |
| 2008/0057024 A1 | 3/2008 | Zhang et al. |
| 2008/0063620 A1 | 3/2008 | Cohn et al. |
| 2008/0069865 A1 | 3/2008 | Southard et al. |
| 2008/0071234 A1 | 3/2008 | Kelch et al. |
| 2008/0086110 A1 | 4/2008 | Galdonik et al. |
| 2008/0095736 A1 | 4/2008 | Pathak et al. |
| 2008/0097295 A1 | 4/2008 | Makower et al. |
| 2008/0112921 A1 | 5/2008 | Chamness |
| 2008/0154250 A1 | 6/2008 | Makower et al. |
| 2008/0160064 A1 | 7/2008 | Capelli et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 69723429 T2 | 4/2004 |
| DE | 60210441 T2 | 11/2006 |
| EP | 0100148 A1 | 2/1984 |
| EP | 0117632 A2 | 9/1984 |
| EP | 0161865 A2 | 11/1985 |
| EP | 0317780 A1 | 5/1989 |
| EP | 0358302 A2 | 3/1990 |
| EP | 0484387 | 2/1991 |
| EP | 0955969 | 1/1997 |
| EP | 0842268 | 2/1997 |
| EP | 0894004 | 9/1997 |
| EP | 0939639 | 1/1998 |
| EP | 1014998 | 1/1999 |
| EP | 0943299 A1 | 9/1999 |
| EP | 1038538 A1 | 9/2000 |
| EP | 1244725 | 6/2001 |
| EP | 1208850 A1 | 5/2002 |
| EP | 1325753 A2 | 7/2003 |
| EP | 1327460 A2 | 7/2003 |
| EP | 1383522 | 1/2004 |
| EP | 1018967 B1 | 8/2004 |
| EP | 1457499 A1 | 9/2004 |
| EP | 1488748 A1 | 12/2004 |
| EP | 1712252 A1 | 10/2006 |
| EP | 1738760 A1 | 1/2007 |
| EP | 1832302 A1 | 9/2007 |
| EP | 1223981 B1 | 1/2008 |
| FR | 2812551 A1 | 2/2002 |
| FR | 2899479 A1 | 10/2007 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| GB | 2415382 A | 12/2005 |
| JP | 4129536 | 4/1992 |
| SG | 71559 | 4/2002 |
| WO | WO 80/02182 | 10/1980 |
| WO | WO 86/04235 A1 | 7/1986 |
| WO | WO 87/04626 | 8/1987 |
| WO | WO 90/10424 | 9/1990 |
| WO | WO 91/01126 A1 | 2/1991 |
| WO | WO 93/09727 | 5/1993 |
| WO | WO 94/20041 | 9/1994 |
| WO | WO 94/22455 A1 | 10/1994 |
| WO | WO 94/28935 A1 | 12/1994 |
| WO | WO 96/05873 | 2/1996 |
| WO | WO 9605873 A1 * | 2/1996 |
| WO | WO 96/17606 A1 | 6/1996 |
| WO | WO 96/35416 A1 | 11/1996 |
| WO | WO 96/38136 A1 | 12/1996 |
| WO | WO 96/40771 A1 | 12/1996 |
| WO | WO 97/02794 A1 | 1/1997 |
| WO | WO 97/05241 A2 | 2/1997 |
| WO | WO 97/05285 A2 | 2/1997 |
| WO | WO 97/18007 | 5/1997 |
| WO | WO 97/34626 A1 | 9/1997 |
| WO | WO 97/36553 | 10/1997 |
| WO | WO 97/37002 A1 | 10/1997 |
| WO | WO 98/02171 A1 | 1/1998 |
| WO | WO 99/02168 A1 | 1/1999 |
| WO | WO 99/13793 | 3/1999 |
| WO | WO 00/09087 A1 | 2/2000 |
| WO | WO 00/45804 A2 | 8/2000 |
| WO | WO 00/56374 A1 | 9/2000 |
| WO | WO 01/12203 A1 | 2/2001 |
| WO | WO 01/30386 A1 | 5/2001 |
| WO | WO 01/51054 A2 | 7/2001 |
| WO | WO 01/70199 A1 | 9/2001 |
| WO | 01/85248 A1 | 11/2001 |
| WO | WO 01/82863 A2 | 11/2001 |
| WO | WO 01/82937 A1 | 11/2001 |
| WO | WO 01/85248 A1 | 11/2001 |
| WO | WO 01/85664 A2 | 11/2001 |
| WO | WO 02/09729 A2 | 2/2002 |
| WO | WO 02/062335 A2 | 8/2002 |
| WO | WO 02/072020 A2 | 9/2002 |
| WO | WO 02/085384 A2 | 10/2002 |
| WO | WO 02/085385 A2 | 10/2002 |
| WO | WO 02/085386 A2 | 10/2002 |
| WO | WO 02/085387 A2 | 10/2002 |
| WO | WO 03/028590 A1 | 4/2003 |
| WO | WO 03/066705 A1 | 8/2003 |
| WO | WO 03/068245 A1 | 8/2003 |
| WO | WO 2004/002456 A1 | 1/2004 |
| WO | WO 2004/009147 A1 | 1/2004 |
| WO | WO 2004/009227 A2 | 1/2004 |
| WO | WO 2004/015130 A2 | 2/2004 |
| WO | WO 2004/019876 A2 | 3/2004 |
| WO | WO 2004/020011 A1 | 3/2004 |
| WO | WO 2004/028548 A2 | 4/2004 |
| WO | WO 2004/037311 A2 | 5/2004 |

(56) References Cited

FOREIGN PATENT DOCUMENTS

| | | |
|---|---|---|
| WO | WO 2004/037334 A1 | 5/2004 |
| WO | WO 2004/041346 A1 | 5/2004 |
| WO | WO 2004/091592 A2 | 10/2004 |
| WO | WO 2004/110347 A2 | 12/2004 |
| WO | WO 2005/027957 A1 | 3/2005 |
| WO | WO 2005/039489 A2 | 5/2005 |
| WO | WO 2005/039537 A1 | 5/2005 |
| WO | WO 2005/041987 A1 | 5/2005 |
| WO | WO 2005/044285 A1 | 5/2005 |
| WO | WO 2005/046746 A2 | 5/2005 |
| WO | WO 2005/055950 A2 | 6/2005 |
| WO | WO 2005/058294 A1 | 6/2005 |
| WO | WO 2005/065079 A2 | 7/2005 |
| WO | WO 2005/077347 | 8/2005 |
| WO | WO 2005/082341 A2 | 9/2005 |
| WO | WO 2005/089778 A1 | 9/2005 |
| WO | WO 2005/110505 A2 | 11/2005 |
| WO | WO 2005/117755 A2 | 12/2005 |
| WO | WO 2005/123170 A1 | 12/2005 |
| WO | WO 2006/005939 A1 | 1/2006 |
| WO | WO 2006/019844 A1 | 2/2006 |
| WO | WO 2006/020180 A2 | 2/2006 |
| WO | WO 2006/028836 A1 | 3/2006 |
| WO | WO 2006/031922 A2 | 3/2006 |
| WO | WO 2006/055940 A2 | 5/2006 |
| WO | WO 2006/059237 A1 | 6/2006 |
| WO | WO 2006/063350 A2 | 6/2006 |
| WO | WO 2007/008927 A2 | 1/2007 |
| WO | WO 2007/014285 A2 | 2/2007 |
| WO | WO 2007/015964 A1 | 2/2007 |
| WO | WO 2007/019439 A2 | 2/2007 |
| WO | WO 2007/056316 A2 | 5/2007 |
| WO | WO 2007/060433 A1 | 5/2007 |
| WO | WO 2007/067621 A2 | 6/2007 |
| WO | WO 2007/067623 A2 | 6/2007 |
| WO | WO 2007/067625 A2 | 6/2007 |
| WO | WO 2007/067637 A2 | 6/2007 |
| WO | WO 2007/082331 A1 | 7/2007 |
| WO | WO 2007/084610 A2 | 7/2007 |
| WO | WO 2007/111925 A2 | 10/2007 |
| WO | WO 2007/124132 A2 | 11/2007 |
| WO | WO 2007/133618 A2 | 11/2007 |
| WO | WO 2007/133644 A2 | 11/2007 |
| WO | WO 2007/142683 A2 | 12/2007 |
| WO | WO 2008/006658 A1 | 1/2008 |
| WO | WO 2008/036361 A2 | 3/2008 |
| WO | WO 2008/048481 A2 | 4/2008 |
| WO | WO 2008/049029 A2 | 4/2008 |
| WO | WO 2008/063943 A2 | 5/2008 |
| WO | WO 2008/080128 A1 | 7/2008 |
| WO | WO 2008/086397 A2 | 7/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989 pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ. . Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, "*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

PCT International Search Report and Written Opinion Issued on Jul. 16, 2008 in PCT International Application No. PCT/US 08/00596.

Non-Final Office Action dated Nov. 19, 2003 for U.S. Appl. No. 10/075,743.
Response filed Mar. 9, 2006 for U.S. Appl. No. 10/075,743.
Final Office Action dated Jun. 2, 2004 for U.S. Appl. No. 10/075,743.
Response filed Nov. 23, 2004 for U.S. Appl. No. 10/075,743.
Non-Final Office Action dated Dec. 16, 2004 for U.S. Appl. No. 10/075,743.
Response filed Apr. 18, 2005 for U.S. Appl. No. 10/075,743.
Notice of Allowance dated Jun. 27, 2005 for U.S. Appl. No. 10/075,743.
RCE/Response filed Jan. 9, 2006 for U.S. Appl. No. 10/075,743.
Notice of Allowance date mailed Jan. 20, 2006 for U.S. Appl. No. 10/075,743.
Non-Final Office Action dated Sep. 14, 2007 for U.S. Appl. No. 11/409,116.
Response filed Jan. 8, 2008 for U.S. Appl. No. 11/409,116.
Final Office Action dated Mar. 27, 2008 for U.S. Appl. No. 11/409,116.
Response filed Apr. 11, 2008 for U.S. Appl. No. 11/409,116.
Advisory Action before the Filing of an Appeal Brief dated Jun. 2, 2008 for U.S. Appl. No. 11/409,116.
Notice of Allowance dated Apr. 14, 2009 for U.S. Appl. No. 11/409,116.
RCE filed on Jun. 4, 2009 for U.S. Appl. No. 11/409,116.
Non-Final Office Action dated Sep. 3, 2009 for U.S. Appl. No. 11/409,116.
Examiners Interview Summary dated Dec. 29, 2009 for U.S. Appl. No. 11/409,116.
Response filed Dec. 31, 2009 for U.S. Appl. No. 11/409,116.
Notice of Allowance date mailed Feb. 17, 2010 for U.S. Appl. No. 11/409,116.
Non-Final Office Action dated Oct. 1, 2008 for U.S. Appl. No. 11/657,887.
Response filed Dec. 22, 2008 for U.S. Appl. No. 11/657,887.
Non-Final Action dated Jun. 23, 2009 for U.S. Appl. No. 11/657,887.
Response filed Sep. 18, 2009 for U.S. Appl. No. 11/657,887.
Notice of Allowance dated Dec. 11, 2009 for U.S. Appl. No. 11/657,887.
Non-Final Office Action dated Dec. 3, 2003 for U.S. Appl. No. 10/161,076.
Response filed Jun. 2, 2004 for U.S. Appl. No. 10/161,076.
RCE filed Sep. 28, 2004 for U.S. Appl. No. 10/161,076.
Final Office Action dated Dec. 15, 2004 for U.S. Appl. No. 10/161,076.
RCE and response filed Jun. 15, 2005 for U.S. Appl. No. 10/161,076.
Non-Final Office Action dated Sep. 7, 2005 for U.S. Appl. No. 10/161,076.
Response filed Mar. 7, 2006 for U.S. Appl. No. 10/161,076.
Final Office Action dated May 24, 2006 for U.S. Appl. No. 10/161,076.
RCE and response filed Nov. 21, 2006 for U.S. Appl. No. 10/161,076.
Non-Final Office Action dated Feb. 12, 2007 for U.S. Appl. No. 10/161,076.
Non-Final Office Action dated Sep. 14, 2007 for U.S. Appl. No. 10/161,076.
Response filed Mar. 14, 2008 for U.S. Appl. No. 10/161,076.
Final Office Action dated Jun. 20, 2008 for U.S. Appl. No. 10/161,076.
Notice of Appeal filed Dec. 22, 2008 for U.S. Appl. No. 10/161,076.
RCE/Amendment filed Jul. 22, 2009 for U.S. Appl. No. 10/161,076.
Non-Final Action dated Aug. 25, 2009 for U.S. Appl. No. 10/161,076.
Response Filed Feb. 25, 2010 for U.S. Appl. No. 10/161,076.
Re-Submission filed Mar. 15, 2010 of Feb. 25, 2010 Response to Office Action for U.S. Appl. No. 10/161,076.
Final Rejection date mailed Apr. 8, 2010 for U.S. Appl. No. 10/161,076.
RCE/Response filed Oct. 8, 2010 for U.S. Appl. No. 10/161,076.
Final Office Action date mailed Oct. 25, 2010 for U.S. Appl. No. 10/161,076.
Letter withdrawing official action date mailed Nov. 3, 2010 for U.S. Appl. No. 10/161,076.
Response filed Jan. 1, 2011 for U.S. Appl. No. 10/161,076.
Non-Final Office Action date mailed Feb. 16, 2011 for U.S. Appl. No. 10/161,076.
Response filed Aug. 16, 2011 for U.S. Appl. No. 10/161,076.
Final Office Action date mailed Oct. 13, 2011 for U.S. Appl. No. 10/161,076.
Non-Final Office Action date mailed Feb. 11, 2011 for U.S. Appl. No. 12/758,460.
Response filed Apr. 21, 2011 for U.S. Appl. No. 12/758,460.
Non-Final Office Action date mailed Mar. 9, 2011 for U.S. Appl. No. 12/828,117.
Response filed Jun. 29, 2011 for U.S. Appl. No. 12/828,117.
Notice of Allowance date mailed Aug. 26, 2011 for U.S. Appl. No. 12/828,117.
Extended European Supplementary Search for European Patent Application 08724562.7 Mailed Jul. 7, 2012.

\* cited by examiner

BIOCOMPATIBLE WOUND DRESSING

CROSS REFERENCE TO RELATED APPLICATIONS

This application is a continuation of U.S. patent application Ser. No. 12/828,117 filed on Jun. 30, 2010, now U.S. Pat. No. 8,084,664 which is a continuation of U.S. patent application Ser. No. 11/409,116 filed on Apr. 21, 2006, now U.S. Pat. No. 7,763,769, which is a continuation of U.S. patent application Ser. No 10/075,743 filed on Feb. 14, 2002, now U.S. Pat. No. 7,070,584, which claims the benefit of and priority to U.S. Provisional Application No. 60/269,657, filed Feb. 16, 2001. All of the above-mentioned applications are hereby incorporated by reference.

BACKGROUND OF THE INVENTION

1. Field of the Invention

This invention relates generally to wound dressings commonly associated with the vacuum induced healing of open wounds. More particularly, the present invention relates to a wound dressing, having a cell growth enhancing porous lattice, matrix, or scaffold, or a bioabsorbable layer as part of the dressing to enhance the wound healing.

2. Description of Related Art

Vacuum induced healing of open wounds has recently been popularized by Kinetic Concepts, Inc. of San Antonio, Tex., by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261,893, issued Nov. 16, 1993, and U.S. Pat. No. 5,527,293, issued Jun. 18, 1996, the disclosures of which are incorporated herein by this reference. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997, respectively, the disclosures of which are incorporated by reference as though fully set forth herein.

Substantial work has also been performed relating to the creation of bioabsorbable and includable, cell growth enhancing matrices, lattices, or scaffolds. Exemplary U.S. patents known to applicant include Kemp et al. U.S. Pat. No. 5,256,418 issued Oct. 26, 1993; Chatelier et al. U.S. Pat. No. 5,449,383 issued Sep. 12, 1995; Bennett et al. U.S. Pat. No. 5,578,662 issued Nov. 26, 1996; and two patents issued to Yasukawa et al. U.S. Pat. No. 5,629,186 issued May 13, 1997 and U.S. Pat. No. 5,780,281 issued Jul. 14, 1998, both from a common parent application; the disclosures of which are incorporated by reference herein.

As is well known to those of ordinary skill in the art, closure of surface wounds involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient bloodflow, the epithelial and subcutaneous tissues surrounding the wound not only receive diminished oxygen and nutrients, but also are less able to successfully fight bacterial infection and thus are less able to naturally close the wound. Until the advent of vacuum induced therapy, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples may cause very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return.

While V.A.C.® therapy has been highly successful in the promotion of wound closure, healing many wounds previously thought largely untreatable, some difficulty remains. Because the very nature of V.A.C.® therapy dictates an atmospherically sealed wound site, the therapy must often be performed to the exclusion of other beneficial, and therefore desirable, wound treatment modalities. One of these hitherto excluded modalities is the encouragement of cell growth by the provision of an in situ cell growth-enhancing matrix.

Additional difficulty remains in the frequent changing of the wound dressing. As the wound closes, binding of cellular tissue to the wound dressing may occur. Use of traditional V.A.C.® therapy necessitates regular changing of the dressing. Reckless dressing changes can result in some tissue damage at the wound site if cellular tissue has grown excessively into the dressing.

Accordingly a primary object of the present invention is to provide an improved wound dressing for vacuum induced healing therapy, which overcomes the problems and limitations of the prior art.

A further object of the present invention is to provide a dressing that is also readily adaptable to a variety of wound sizes and shapes and that requires no inordinate modification of know procedures for administration of V.A.C.® therapy.

Another object is to provide a pad that enables the concurrent application of vacuum induced healing and cell growth enhancement in the treating of a wound by providing a bioabsorbable, or includable, porous cell growth enhancing matrix substrate thereupon.

An additional object of the present invention is to allow for controlled application of growth factors or other healing factors, which could be embedded in the dressing or introduced into the dressing through a port or other connector fitting.

Still another object of the present invention is to provide a fully and/or partially bioabsorbable wound dressing that minimizes disruption of the wound site during dressing changes.

A yet further object of the present invention is to provide such a dressing that is economical and disposable, but also safe for general patient use.

BRIEF SUMMARY OF THE INVENTION

In accordance with the foregoing objects, the present invention generally comprises a foam pad for insertion substantially into the wound site and a wound drape for sealing enclosure of the foam pad at the wound site. The foam pad, comprised of a foam having relatively few open cells in contact with the areas upon which cell growth is to be encouraged so as to avoid unwanted adhesions, but having sufficiently numerous open cells so that drainage and V.A.C.® therapy may continue unimpaired, is placed in fluid communication with the vacuum source for promotion of fluid drainage, as known in the art. The foam pad is further comprised of a cell growth lattice, matrix, or scaffolding, all of which have been used in the art to describe similar constructs, is noninvasive to the known V.A.C.® therapy and requires no modification thereof. Additionally, or alternatively, the foam pad may be comprised of bioabsorbable polymers.

The foam pad of the present invention is provided with a bioabsorbable, or includable, fibrous growth-enhancing matrix. Numerous suitable materials for this purpose are known the art, including collagen, dissolvable nylon, soluble plastics, and fibrous ceramic material. An exemplary fibrous ceramic material that may be utilized is an ultra-low density fused-fibrous ceramic manufactured by Materials Evolution and Development USA, Inc., under the trade name P.R.I.M.M.™ (Polymeric Rigid Inorganic Matrix Material), and further described in U.S. Pat. No. 5,951,295 issued on Sep. 14, 1999 to Lyles, et al., which is incorporated herein by reference. Additional materials may include alginates, fibrin gels, fused fibers and other similar materials utilized by those skilled in the art, that are capable of providing an invadable space and scaffolding for cellular growth. Alternatively, the growth-enhancing matrix may be non-fibrous, such as a gel-like growth-enhancing matrix. This matrix comprises a cell growth enhancing substrate that is up to over 90% open space. The fibers, or other particles, and spaces create nooks and crannies that provide an excellent environment to enhance cell growth, and thus further the process envisioned by the vacuum induced healing process.

Upon placement of the pad, having the cell growth enhancing substrate matrix embedded therein, an airtight seal is formed over the wound site to prevent vacuum leakage. In use the V.A.C.® therapy is conducted as known and, if desired, cell growth enhancement therapy is added by simply placing the matrix on the pad that is located within the wound. Given the addition of a suitable surface to which the fibrous lattice may be attached, the cell growth is channeled into the most desirable form and location, but is kept away from the pad itself. Utilization of bioabsorbable branched polymers in the pad itself, in addition to, or in place of the cell growth enhancing matrix, can allow the pad to remain in place during the healing process. As cell growth continues, the pad is absorbed, and there is no need to remove the pad.

An alternative embodiment comprises use of bioabsorbable branched polymers within a layer of the pad adjacent the wound, such that upon removal of the pad during dressing changes, the bioabsorbably branched polymer layer is left behind, leaving the wound site itself undisturbed. Additionally, the cell growth enhancing substrate matrix may be incorporated within the polymer layer to further enhance cellular growth at the wound site.

Accordingly, cell growth enhancement therapy may be conveniently combined with existing V.A.C.® therapies, without loss of V.A.C.® therapy performance and without inconvenience or overly increased cost.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims that may be drawn hereto.

The present invention is a biocompatible wound dressing for use with negative pressure therapy. The term "wound" as used herein, may include burns, incisional wounds, excisional wounds, ulcers, traumatic wounds, and chronic open wounds. As used herein, the term "pad" refers to foam, screens, and other porous-like materials. The term "conventional pad" refers to polyurethane (PU) or polyvinylalcohol (PVA) foams commonly used with V.A.C.® therapy. The term "V.A.C.® therapy" as used herein, refers to negative pressure wound therapy as commercialized by the assignee or its parent, and further described in the aforementioned patents and patent applications.

Figure 1:
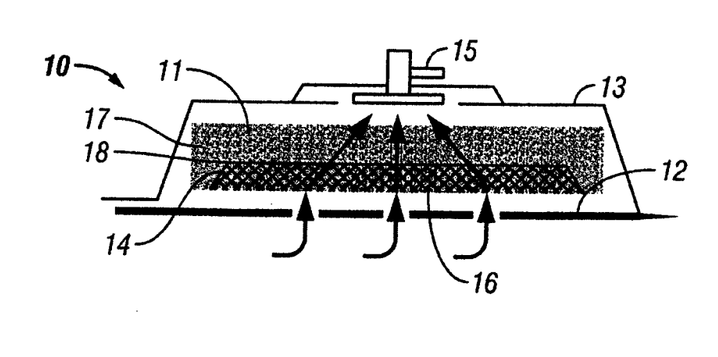
FIG. 1 shows, in partially cut away perspective view, the preferred embodiment of the present invention as applied to a mammalian wound site.

Referring now to the figures, the present invention 10 is shown to generally comprise a foam pad 11 for insertion substantially into the wound site 12 and a wound drape 13 for sealing enclosure of the foam pad 11 at the wound site 12. According to the invention, the foam pad 11 is modified to contain a cell growth-enhancing matrix, or lattice 14, whereby a desired highly porous cell growth enhancing substrate may be directed into and about the wound site 12. After insertion into the wound site 12 and sealing with the wound drape 13, the foam pad 11 is placed in fluid communication with a vacuum source for promotion of fluid drainage, as known to those of ordinary skill in the art. Foam pad 11 is modified from prior art pads in that the pad 11 comprises matrix 14 that is noninvasive to the known V.A.C.® therapy and therefore requires no modification thereof.

According to the preferred embodiment of the present invention, the foam pad 11, wound drape 13 and vacuum source are implemented as known in the prior art, with the exception of those modifications of the foam pad 11 detailed further herein. Each of these components is detailed in U.S. patent application Ser. No. 08/951,832 filed Oct. 16, 1997, which is a Continuation of U.S. patent application Ser. No. 08/517,901 filed Aug. 22, 1995, which is a Continuation-in-part of U.S. patent application Ser. No. 08/293,854 filed Aug. 22, 1994. By this reference, the full specification of U.S. patent application Ser. No. 08/951,832 ("the '832 application"), including the claims and the drawings, is incorporated as though fully set forth herein.

As detailed in the '832 application, the foam pad 11 preferably comprises a highly reticulated, open-cell polyurethane or polyether foam for good permeability of wound fluid while under suction. As also detailed in the '832 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '832 application also details the wound drape 13, which preferably comprises an elastomeric material at least peripherally covered with an pressure sensitive, acrylic adhesive for sealing application over the wound site 12.

According to the preferred method of the present invention, those components as are described in the '832 application are generally employed as shown in the art with the exception that the foam pad 11 is provided with a matrix 14. This matrix 14 is shown to comprise porous material 16 that has been formed into a plurality of sections 17. The material 16 is implanted in the foam pad 11 at the base 18 of the pad 11. Because it is necessary to trim the foam pad 11 in preparation for V.A.C.® therapy wound treatment, material 16 preferably is placed in the central portion of pad 11. Applicant does not intend to limit itself to a regular or symmetrical arrangement of material 16 or sections 17 by use of the term "matrix".

Alternatively, or in addition to the preferred embodiment, the foam pad may be comprised of bioabsorbable branched polymers alone (not shown), or in combination with the matrix 14.

Upon placement of the pad 11, having the matrix 14 embedded therein, and/or protruding therefrom, and/or comprised of bioabsorbable branched polymers, the wound drape 13 is applied over the pad to form an airtight seal over the wound site. In use, the V.A.C.® therapy is conducted as known and, if desired, cell growth enhancement therapy is added by simply providing the matrix 14 comprising material 16. In this manner, cell growth enhancement therapy may be conveniently combined with existing V.A.C.® therapies, without loss of V.A.C.® therapy performance and without inconvenience or overly increased cost.

Example I

The above described open celled foam is formed into a pad. The general principles set forth in U.S. Pat. No. 5,795,584 issued to Totakura et al. on Aug. 18, 1998 at Col. 5 lines 5-42, are followed to create a structure superimposed on the bottom of the pad. Holes are placed in those portions of the non-bioabsorbable substrate relatively remote from the bioabsorbable cell growth enhancing matrix substrate. The matrix covers a portion of the pad located within the boundaries of the wound being treated. The pad is then completely covered by an airtight drape, and subjected to sub atmospheric pressure, as is the standard practice for utilizing V.A.C.® therapy. The matrix is absorbed within the expected useful life of the pad, so, that when the pad is removed, the matrix has been absorbed, and the growing cells are not disturbed. The pad is replaced, if necessary, either by a conventional pad or by a matrix containing pad, as deemed therapeutically necessary.

Example II

A conventional pad is selected. A collagen cell growth matrix is applied to a portion of the bottom thereof The general principles of V.A.C.® therapy are followed, with the matrix containing pad substituted for a conventional pad. During the expected duty cycle of the pad, the collagen matrix is absorbed by the growing cells, so that when the pad is removed, the matrix has been absorbed, and the growing cells are not disturbed. The pad is replaced, if necessary, either by a conventional pad or by a matrix containing pad, as deemed therapeutically necessary.

Example III

The procedure set forth in EXAMPLE II is followed. However, an ultra-low density fused-fibrous ceramic, sometimes referred to under the trademark P.RI.M.M., is substituted for the collagen matrix thereof. The general principles of V.A.C.® therapy are followed. During the expected duty cycle of the pad, the ultra-low density fused-fibrous ceramic is absorbed by the growing cells, so, that when the pad is removed, the ultra-low density fused-fibrous ceramic had been absorbed, and the growing cells were not disturbed. The pad is replaced, if necessary, either by a conventional pad or by a matrix containing pad, as deemed therapeutically necessary.

Example IV

Many suitable bioabsorbable materials have been used for sutures, surgical implements, and the like. A small sample of these materials are set forth in the following U.S. patents, to wit: U.S. Pat. No. 5,997,568, issued to Lin on Dec. 7, 1999 and the following patents issued in 1999 to Roby et al.: U.S. Pat. Nos. 5,914,387; 5,902,874 and 5,902,875. A selected one or more of these, or similar materials, are placed upon a conventional pad. The general principles of V.A.C.® therapy are followed. During the expected duty cycle of the pad, the bioabsorbable material is absorbed by the growing cells, so, that when the pad is removed, the bioabsorbable material had been absorbed, and the growing cells were not disturbed. The pad is replaced, if necessary, either by a conventional pad or by a matrix containing pad, as deemed therapeutically necessary.

Example V

A bioabsorbable branched polymer, similar to that described in U.S. Pat. No. 5,578,662 issued to Bennet et al., forms the pad. The general principles of V.A.C.® therapy are followed with the bioabsorbable branched polymer pad substituted for the conventional pad. During the expected duty cycle of the pad, the pad is absorbed by the growing cells, so that there is no need to replace the pad and disturb the wound site. If further treatment is deemed necessary, a conventional pad, or an additional matrix containing pad, or an additional bioabsorbable branched polymer pad may be placed in the wound site, and V.A.C.® therapy continued.

While the foregoing description is exemplary of the preferred embodiment of the present invention, those of ordinary skill in the relevant arts will recognize the many variations, alterations, modifications, substitutions and the like are readily possible, especially in light of this description and the accompanying drawings. In any case, because the scope of the present invention is much broader than any particular embodiment, the foregoing detailed description should not be construed as a limitation of the scope of the present invention, which is limited only by the claims that are drawn hereto.

We claim:

1. A biocompatible wound dressing comprising:
   a pad comprising an open-cell porous foam adapted to be in fluid communication with a vacuum source for delivering a negative pressure to the pad; and
   a material implanted in the pad in fluid communication with the pad, the material having a surface adapted to be placed in contact with a tissue site where new cell growth is desired and having an invadable space for cellular growth from the tissue site into the invadable space, wherein the invadable space of the material remains in place following treatment.

2. The biocompatible wound dressing according to claim 1 further comprising:
   a tube fluidly connecting the pad to the vacuum source.

3. The biocompatible wound dressing according to claim 1, wherein the material is bioabsorbable.

4. The biocompatible wound dressing according to claim wherein the material is a bioabsorbable branched polymer.

5. The biocompatible wound dressing according to claim 1 further comprising a seal removably adhered to the pad.

6. The biocompatible wound dressing according to claim 1, wherein the material is porous to allow distribution of negative pressure to the tissue site.

7. The biocompatible wound dressing according to claim 1 further comprising a canister fluidly connected between the pad and the vacuum source.

8. The biocompatible wound dressing according to claim 1, wherein the material is selected from the group consisting of collagen, dissolvable nylon, soluble plastics, fibrous ceramics, alginates, fibrin gels, fused fibers, and branched polymers.

9. The biocompatible wound dressing according to claim 1, wherein the negative pressure is sub-atmospheric pressure.

10. A biocompatible wound dressing comprising:
    a foam pad adapted to be in fluid communication with a vacuum source for delivering a negative pressure to the foam pad; and
    a matrix embedded with in a portion of the pad and having a surface adapted to be placed in contact with a tissue site where new cell growth is desired, the matrix having an invadable space for cellular growth from the tissue site, wherein the matrix remains in place following treatment.

11. The biocompatible wound dressing according to claim 10, wherein the matrix is collagen.

12. The method according to claim 10 further comprising:
    positioning a second scaffold in contact with the scaffold.

13. A method of promoting new cell growth at a wound site comprising:
    positioning a scaffold in contact with the wound site;
    delivering a negative pressure to the wound site through the scaffold to induce new cell growth from the wound site into the scaffold; and
    allowing the scaffold to remain in place at the wound site after delivery of negative pressure to promote new cell growth.

14. The method according to claim 13 wherein the scaffold is not bioabsorbable.

15. The method according to claim 13 further comprising:
    positioning a pad having a bioabsorbable or includable component and a non-bioabsorbable component such that the bioabsorbable or includable component contacts the scaffold; and
    delivering a negative pressure to the pad to promote new cell growth within at least one of the scaffold and the bioabsorbable or includable component of the pad.

16. The method according to claim 15 further comprising:
    removing the non-bioabsorbable component of the pad following delivery of the negative pressure.

17. The method according to claim 13 further comprising:
    covering the wound and the scaffold with a drape to assist in maintaining the negative pressure at the wound.

18. The method according to claim 13, wherein the negative pressure is sub-atmospheric pressure.

19. The method according to claim 13, wherein the scaffold is capable of providing an invadable space and scaffolding for cellular growth.

20. The method according to claim 15, wherein the bioabsorbable component is selected from the group consisting of collagen, dissolvable nylon, soluble plastics, fibrous ceramics, alginates, fibrin gels, fused fibers, and branched polymers.

* * * * *